(12) United States Patent
Blue et al.

(10) Patent No.: US 9,714,565 B2
(45) Date of Patent: Jul. 25, 2017

(54) SLOT TESTER

(71) Applicant: M-I L.L.C., Houston, TX (US)

(72) Inventors: Aaron Blue, Houston, TX (US); John D. Moffitt, Sugar Land, TX (US); Ahmed Said Amer, Houston, TX (US)

(73) Assignee: M-I L.L.C., Houston, TX (US)

( * ) Notice: Subject to any disclaimer, the term of this patent is extended or adjusted under 35 U.S.C. 154(b) by 290 days.

(21) Appl. No.: 14/143,098

(22) Filed: Dec. 30, 2013

(65) Prior Publication Data

US 2014/0182369 A1 Jul. 3, 2014

Related U.S. Application Data

(60) Provisional application No. 61/747,732, filed on Dec. 31, 2012.

(51) Int. Cl.
*E21B 47/06* (2012.01)
*G01N 33/28* (2006.01)

(52) U.S. Cl.
CPC ......... *E21B 47/06* (2013.01); *G01N 33/2823* (2013.01)

(58) Field of Classification Search
CPC ............................ G01N 33/2823; E21B 47/06
USPC ....................................................... 73/152.27
See application file for complete search history.

(56) References Cited

U.S. PATENT DOCUMENTS

| | | | |
|---|---|---|---|
| 1,021,133 A | 3/1912 | Chaloud | |
| 1,471,361 A | 10/1923 | Sarles | |
| 2,449,238 A | 9/1948 | Lightfoot, Jr. | |
| 2,455,486 A | 12/1948 | Hicks | |
| 2,547,797 A | 4/1951 | Torrey et al. | |
| 2,618,151 A | 11/1952 | Leas | |
| 2,646,678 A | 7/1953 | Standing et al. | |
| 2,733,595 A | 2/1956 | Twinning | |
| 2,842,958 A | 7/1958 | Sayre, Jr. et al. | |
| 2,889,836 A | 6/1959 | Maley | |
| 3,172,286 A | 3/1965 | Grubb et al. | |
| 3,289,467 A | 12/1966 | Parker et al. | |

(Continued)

FOREIGN PATENT DOCUMENTS

WO      2009109739 A1      9/2009

OTHER PUBLICATIONS

"Permeability Plugging Apparatus (PPA)", Retrieved from the Internet: http://www.fann.com/fann/products/drilling-fluids-testing/ppa. page, Retrieved on Apr. 22, 2013, 2 pages.

(Continued)

*Primary Examiner* — John Fitzgerald
(74) *Attorney, Agent, or Firm* — Sara M. Hinkley

(57) ABSTRACT

A method for using a drilling fluid test device including a test cell including a perforated plate disposed proximate a first end of the test cell, a piston disposed within the cell, a first chamber formed between the perforated plate and the piston, the first chamber configured to receive lost circulation material (LCM), a second chamber formed between the piston and a second end of the test cell, the piston providing a seal between the first and second chambers, a fluid inlet disposed proximate the second end of the test cell configured to introduce fluid into a second chamber of the test cell, a filtrate outlet disposed proximate the first end of the test cell to discharge filtrate, and a pump in communication with the fluid inlet.

18 Claims, 4 Drawing Sheets

(56) References Cited

U.S. PATENT DOCUMENTS

| | | | |
|---|---|---|---|
| 3,324,712 A * | 6/1967 | Watson | E21B 21/003 138/45 |
| 3,370,707 A | 2/1968 | Nordstrom | |
| 3,401,802 A | 9/1968 | Fann | |
| 3,516,478 A | 6/1970 | Dunn et al. | |
| 3,522,886 A | 8/1970 | Clinton et al. | |
| 3,702,659 A | 11/1972 | Clark | |
| 3,983,743 A | 10/1976 | Olin et al. | |
| 4,287,066 A | 9/1981 | Greutert et al. | |
| 4,375,409 A | 3/1983 | Gentry | |
| 4,397,177 A | 8/1983 | Cain | |
| 4,434,054 A | 2/1984 | Livesey et al. | |
| 4,561,289 A | 12/1985 | Jones | |
| 4,610,158 A | 9/1986 | Lawton | |
| 4,637,876 A | 1/1987 | Dosoudil | |
| 4,640,140 A | 2/1987 | Burghoffer et al. | |
| 4,643,019 A | 2/1987 | Jones | |
| 4,748,849 A | 6/1988 | Jamison et al. | |
| 4,876,007 A | 10/1989 | Naruo et al. | |
| 4,882,055 A | 11/1989 | Stamstad | |
| 4,902,420 A | 2/1990 | Pall et al. | |
| 4,921,712 A | 5/1990 | Malmquist | |
| 5,100,551 A | 3/1992 | Pall et al. | |
| 5,292,437 A | 3/1994 | Ford | |
| 5,492,175 A | 2/1996 | El-Rabaa et al. | |
| 5,763,367 A | 6/1998 | Burts | |
| 5,824,218 A | 10/1998 | Gasser et al. | |
| 6,269,684 B1 | 8/2001 | Maki, Jr. et al. | |
| 6,343,697 B1 | 2/2002 | Hausdorf et al. | |
| 6,543,276 B2 | 4/2003 | Murphy, Jr. et al. | |
| 6,685,759 B2 | 2/2004 | Dahlin et al. | |
| 6,710,019 B1 | 3/2004 | Sawdon et al. | |
| 6,971,448 B2 | 12/2005 | Slabaugh et al. | |
| 8,863,567 B2 * | 10/2014 | Jappy | E21B 21/003 73/61.64 |
| 9,285,355 B2 * | 3/2016 | Murphy | G01N 33/2823 |
| 2006/0223715 A1 | 10/2006 | Svoboda et al. | |
| 2006/0254826 A1 | 11/2006 | Alberthy | |
| 2008/0113879 A1 * | 5/2008 | Way | C09K 8/035 507/117 |
| 2008/0236253 A1 * | 10/2008 | Tehrani | G01N 15/06 73/38 |
| 2009/0291861 A1 | 11/2009 | Sawdon | |
| 2010/0139387 A1 * | 6/2010 | Jamison | E21B 21/003 73/152.25 |
| 2011/0226479 A1 * | 9/2011 | Tippel | E21B 33/138 166/305.1 |
| 2011/0278011 A1 * | 11/2011 | Crainich, Jr. | C04B 40/0092 166/310 |
| 2011/0290012 A1 * | 12/2011 | Jappy | E21B 21/003 73/152.55 |
| 2011/0295509 A1 * | 12/2011 | Huynh | G01N 33/2823 702/12 |
| 2013/0192358 A1 * | 8/2013 | Murphy | E21B 49/008 73/152.05 |

OTHER PUBLICATIONS

Hinkebein, Thomas E., "Static slot testing of conventional lost circulation materials", Sandia National Labs., Albuquerque, NM, Retrieved from the Internet: http://www.osti.gov/bridge/servlets/purl/6471455-RkAMQf/native/6471455.pdf, Retrieved on Apr. 22, 2013, 50 pages.

Extended European Search Report issued in related EP application 13199876.7 on Jun. 3, 2014, 8 pages.

Tehrani, et al., "Designing Fluids for Wellbore Strengthening—Is it an Art?", AADE National Technical Conference and Exhibition, Apr. 10-12, 2007; 12 pages.

International Search Report and Written Opinion issued in PCT/US2008/073712 on Jan. 28, 2009; 6 pages.

* cited by examiner

SLOT TESTER

CROSS REFERENCE

This application claims the benefit of a related U.S. Provisional Application Ser. No. 61/747,732, which was filed on 31 Dec. 2012, entitled "SLOT TESTER," to Blue et al., the disclosure of which is incorporated herein by reference in its entirety.

BACKGROUND

When drilling or completing wells in earth formations, various fluids generally are used in the well for a variety of reasons. The fluid may be either water-based or oil-based. For the purposes herein, such fluid will be referred to as "well fluid." Common uses for well fluids include: lubrication and cooling of drill bit cuffing surfaces while drilling generally or drilling-in (i.e., drilling in a targeted petroliferous formation), transportation of "cuttings" (pieces of formation dislodged by the cutting action of the teeth on a drill bit) to the surface, controlling formation fluid pressure to prevent blowouts, maintaining well stability, suspending solids in the well, minimizing fluid loss into and stabilizing the formation through which the well is being drilled, minimizing fluid loss into the formation after the well has been drilled and during completion operations such as, for example, perforating the well, replacing a tool, attaching a screen to the end of the production tubulars, gravel-packing the well, or fracturing the formation in the vicinity of the well, displacing the fluid within the well with another fluid, cleaning the well, testing the well, fluid used for implacing a packer, abandoning the well or preparing the well for abandonment, and otherwise treating the well or the formation.

A variety of compounds may be added to well fluids to enhance their performance. Among these compounds are fluid loss control agents, which act by coating the walls of the wellbore, as the well is drilled, with a thin layer of low-permeability filtercake. The filtercake helps to reduce the amount of base fluid lost to the formation and prevents undesirable variations in the density and rheology of the drilling fluid. Additionally, the filtercake helps prevent formation damage in the reservoir, which may be caused by blockage of formation pores through invasion of wellbore fluid. Filtercake also provides a barrier to prevent the influx and efflux of drilling fluids between the wellbore and the formation. Suitable fluid loss control additives, for both water-based and oil-based drilling fluids include modified starches, synthetic resins, modified lignites, asphaltic compounds, gilsonites, and a wide range of other polymeric and non-toxic fluid loss control materials. Such fluid loss control agents may be generally used in drilling fluids, or may be used in gel pills used to prevent fluid loss in a particular zone of the wellbore.

The role of the fluid loss characteristics of the well fluid demands that the properties of the well fluid are carefully monitored throughout the operation, and that corrective measures are taken in time to maintain the specifications of the fluids in the operation. Fluid loss is conventionally measured by industry standard American Petroleum Institute ("API") tests. The API tests require the use of a new filter for every test. A new filter necessitates the dismantling and cleaning of the testing device (i.e., a filtration cell) between successive tests. Additionally, both the low-temperature/low-pressure and the high-temperature/high-pressure tests require manual cleaning of the internal chambers of the filtration cells between subsequent tests. Taking apart the filtration cell, cleaning the internal chamber, and replacing the filter between tests may be time consuming, expensive, and may require operator attendance through the entire test.

SUMMARY OF THE DISCLOSURE

In one aspect, embodiments of the present disclosure include a system for testing fluids at a drilling location including a test cell including a perforated plate disposed proximate a first end of the test cell, a piston disposed within the test cell, a first chamber formed between the perforated plate and the piston, the first chamber configured to receive lost circulation material (LCM), a second chamber formed between the piston and a second end of the test cell, the piston providing a seal between the first and second chambers, a fluid inlet disposed proximate the second end of the test cell configured to introduce fluid into a second chamber of the test cell, a filtrate outlet disposed proximate the first end of the test cell to discharge filtrate, and a pump in communication with the fluid inlet.

In another aspect, embodiments of the present disclosure include a method of testing well fluid including configuring a test cell by filling a first chamber disposed within the test cell with lost circulation material ("LCM"), applying a pressure to a piston in the test cell, forcing filtrate to exit the test cell, depositing LCM on a perforated plate within the test cell, incrementally increasing pressure on the piston.

In another aspect, embodiments of the present disclosure include a method including pumping a fluid downhole, determining fluid loss of the fluid pumped downhole, selecting a lost circulation material ("LCM") to pump downhole to reduce fluid loss, the selecting including: filling a test cell with LCM, applying a pressure to LCM within the test cell, incrementally increasing pressure on the test cell, comparing at least one LCM's pressure characteristics to present pressure conditions, and pumping the selected LCM downhole.

This summary is provided to introduce a selection of concepts that are further described below in the detailed description. This summary is not intended to identify key or essential features of the claimed subject matter, nor is it intended to be used as an aid in limiting the scope of the claimed subject matter.

DETAILED DESCRIPTION

Generally, embodiments disclosed herein relate to apparatuses and methods for testing drilling fluids used in subterranean drilling operations. More specifically, embodiments disclosed herein relate to apparatuses and methods for testing drilling fluids containing fluid loss control agents used in subterranean drilling operations. More specifically still, embodiments disclosed herein relate to apparatuses and methods for evaluating fluid loss control agents while drilling on a rig.

Embodiments of the present disclosure may provide for the testing of drilling fluids containing fluid loss control agents in a drilling fluid test system. Those of ordinary skill in the art will appreciate that the apparatuses and methods disclosed herein may be used to test both oil-based and water-based drilling fluids containing various fluid loss control agents, such as, starches, synthetic resins, modified lignites, asphaltic compounds, and gilsonites.

Figure 1:
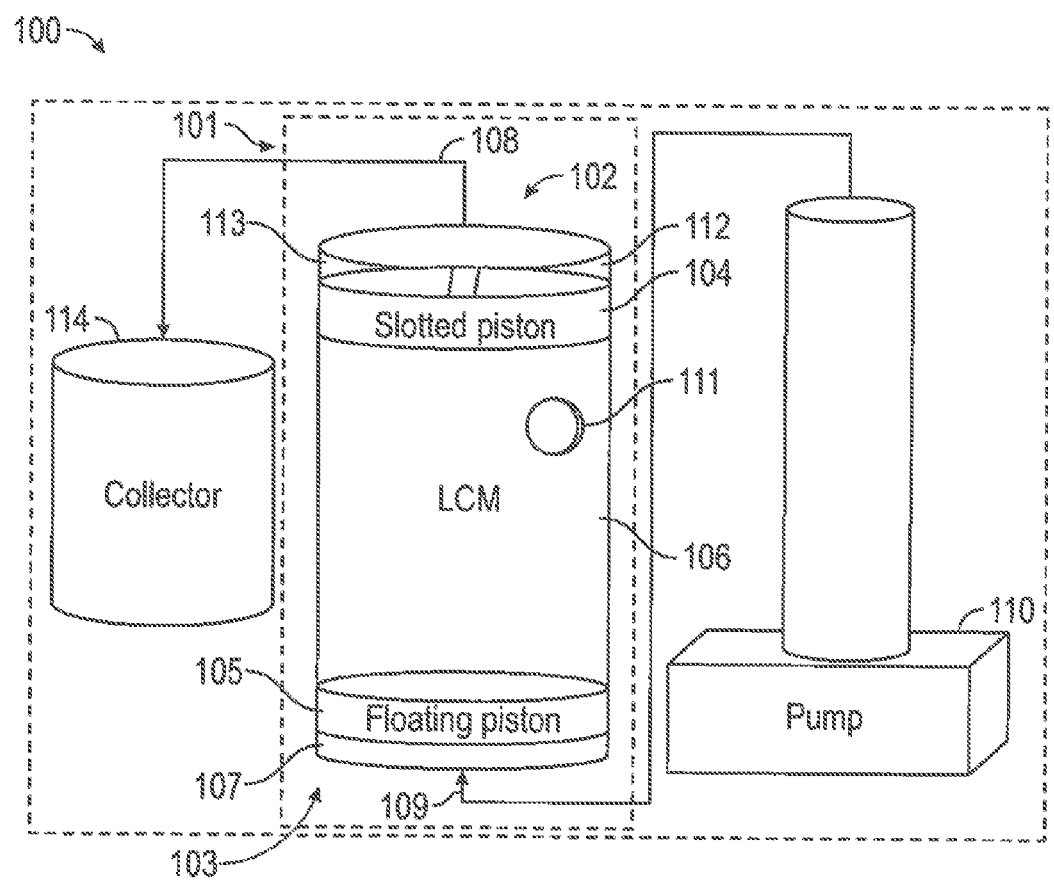
FIG. 1 shows a perspective view of a drilling fluid test system according to embodiments of the present disclosure.

Referring initially to FIG. 1, a perspective view of a drilling fluid test system 100 according to embodiments of the present disclosure is shown. In this embodiment, drilling fluid test system 100 includes a test cell 101 and a pump 110 in fluid communication with the test cell 101. In some embodiments, a filtrate collection vessel 114 may also be in fluid communication with test cell 101. Pump 110 may be any pump known to those of ordinary skill in the art capable of pumping a fluid.

The body of test cell 101 may be any suitable shape known to those of ordinary skill in the art, including but not limited to cylinders and rectangular prisms. The term test cell, as used herein, describes the entire set-up encompassed by the body of the test cell, which may be described by its shape. Test cell 101 includes a first end 102 and a second end 103. A perforated plate 104 is disposed in the test cell 101 proximate the first end 102 such that perforated plate 104 forms a circumferential seal with test cell 101. A piston 105 is located within the test cell such that piston 105 is movably coupled to test cell 101. Piston 105 forms a sealable barrier between a first chamber 106, and a second chamber 107. The first chamber 106 corresponds to the volume formed between perforated plate 104 and piston 105, and the second chamber 107 corresponds to a volume formed between second end 103 and piston 105.

Figure 2A:
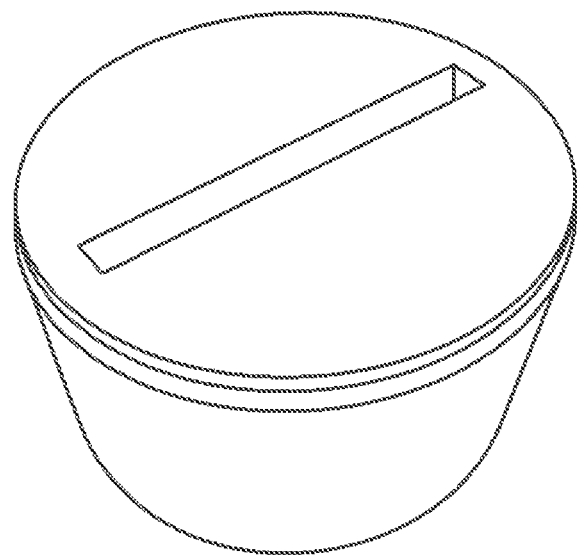
FIG. 2A-2E show various configurations of a perforated plate for a drilling fluid test system in accordance with the present disclosure.
Figure 2B:
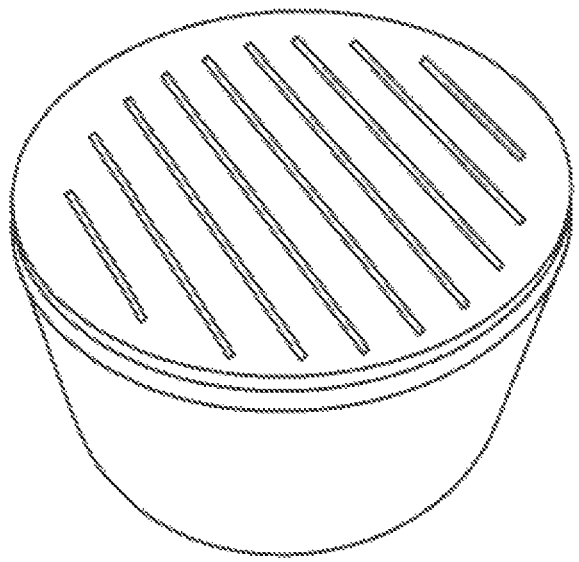
Figure 2C:
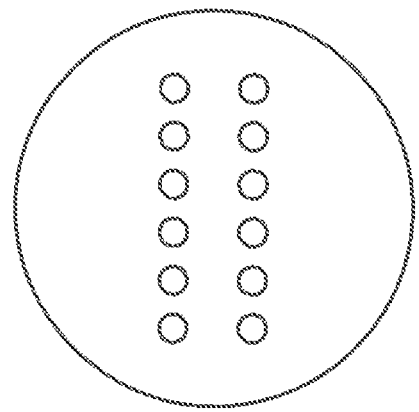
Figure 2D:
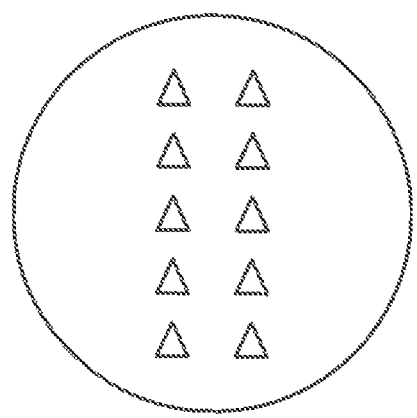
Figure 2E:
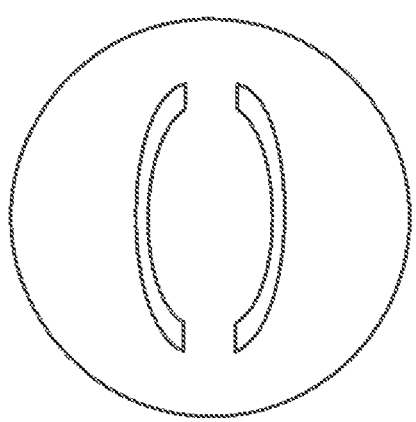

As described herein, perforated plate 104 refers to a plate that includes at least one perforation or opening. This opening may be formed for example, machined, punched, or by any method known in the art. This perforation may have a width, for example, that can range from 1 mm to 5 mm to model a variety of rock formations. Referring to FIGS. 2A-2E, the perforations of perforated plate may be, for example, but not limited to, a slot-like perforation (FIGS. 2A and 2B), a circular perforation (FIG. 2C), or polygonal perforation (FIGS. 2D-2E). Those of ordinary skill in the art will appreciate that the shape of the perforation is not a limitation on the scope of the present disclosure. Further, the number of perforations and the placement or distribution of perforations of the perforated plate may vary without departing from the scope of embodiments disclosed herein. The perforations of the perforated plate may be selected so as to simulate fractures in the formation, for example, thin fractures in the formation may be represented by slot-like perforations as shown in FIG. 2B. Larger fractures may be represented by wider slot-like perforations as shown in FIG. 2A.

In one embodiment, the perforated plate 104 may be securably attached to the test cell 101. Perforated plate 104 may be attached to the cell body 101 using, for example but not limited to, a press fit, screws, rivets, or other mechanical fasteners. In other embodiments, perforated plate 104 may be attached to the test cell 101 using hinges, retainer bars, or other means of attaching components known in the art, such that the first chamber 106, may be easily accessed. In the latter case where the perforated plate is configured to allow easy access to the first chamber 106 a fluid may be introduced from the opening at end 102 when the perforated plate is removed. The fluid may be a lost circulation material (LCM), which when sent downhole during drilling serves to prevent fluid loss to the surrounding rock by forming a filtercake on cracks in the rock formation being drilled.

Those of ordinary skill in the art will appreciate that the specific type of attachment is not a limitation on the scope of the present disclosure. Additionally, a seal may be disposed around the circumference of the perforated plate to provide a seal between the perforated plate and an inner surface of the test cell 101. For example, an o-ring may be disposed around the circumference of the perforated plate.

In some embodiments, a spacer ring 112 may be disposed near the first end 102. The spacer ring 112 may be disposed such that a third chamber 113 may be formed between the perforated plate 104 and the first end 102. The spacer ring 112 may be, for example but not limited to, an O-ring, a cylindrical ring, an end cap, or any other spacing device known in the art. In some aspects the spacer ring 112 may be attached to the test cell 101 using screws, rivets, or other mechanical fasteners. In other aspects, the spacer ring 112 may be configured such that it may easily be detached from the test cell 101 using, for example, a threaded engagement or other similar engagements known in the art. In other aspects, perforated plate 104 may be coupled to a lower end of spacer ring 112 using, for example, screws, welding, rivets, or mechanical fasteners known in the art, such that perforated plate 104 is also removably coupled to the test cell 101.

The test cell 101 includes an inlet and an outlet to provide fluid communication between test cell 101 and other components of test device 100. In one embodiment, a first fluid inlet 109 may be disposed proximate the second end 103. First fluid inlet 109 may be disposed anywhere proximate second end 103 such that a fluid may be introduced to second chamber 107. In some embodiments a first end cap (not shown) may be sealably coupled to the second end 103, such that the first end cap defines an end of the second chamber 107. For example, one end cap may be threadedly coupled to second end 103 and include an o-ring or any seal known in the art. In such an embodiment, the first fluid inlet 109 may be disposed on the first end cap such that a fluid may be introduced to second chamber 107. This fluid may be any water-based or oil-based fluid used by those skilled in the art. Optionally, first fluid inlet may be in communication with pump 110. In select embodiments, first fluid inlet 109 may be in fluid communication with additional components such as, for example, remote-controlled pressure regulator valves (not shown) that may be used to regulate the pressure of chamber 107. Additional components coupled to fluid inlet 109 or pump 110 may include pressure gauges (not shown), relief valves (not shown), and other components used to monitor pressure of testing cells known to those of ordinary skill in the art.

Embodiments of test cell 101 may further include a filtrate outlet 108 disposed proximate the first end 102 to discharge a filtrate. In some embodiments a second end cap (not shown) may be sealably coupled to the first end 102, such that the second end cap defines an end of a third chamber 113. For example, the end cap may be threadedly coupled to first end 102 and include an o-ring or any seal known in the art. In such an embodiment, the filtrate outlet 108 may be disposed on the second end cap such that the filtrate that collects in the third chamber 113 may be discharged via the filtrate outlet 108. In select embodiments a filtrate collection vessel 114 may be coupled to filtrate outlet 108 to collect the filtrate exiting test cell 101. A device (not shown) may be coupled to filtrate outlet 108 or filtrate collection vessel 114 in order to monitor a filtrate property such as flow rate, volume, or material composition of the filtrate. The device may be any sensor known to those of ordinary skill in the art such that the specific type monitoring device is not a limitation on the scope of the present disclosure.

In certain embodiments a second fluid inlet 111 may be disposed proximate the first chamber 106 such that fluid may be introduced to first chamber 106 prior to applying pressure to piston 105. In embodiments where the perforated plate is not configured to be removable, a fluid may be introduced into the first chamber 106 through the fluid inlet 111. A LCM test fluid may be added to the first chamber 106. Fluid inlet 111 may also be used to introduce cleaning fluid to second chamber 106 once testing is concluded.

In certain embodiments a second fluid inlet 111 may be disposed proximate the first chamber 106 such that fluid may be introduced to first chamber 106 prior to applying pressure to piston 105. In embodiments where the perforated plate is not configured to be removable, a fluid may be introduced into the first chamber 106 through the fluid inlet 111. A LCM test fluid may be added to the first chamber 106. Fluid inlet III may also be used to introduce cleaning fluid to first chamber 106 once testing is concluded.

In certain embodiments, test cell 101 and perforated plate 104 and piston 105 may be formed from stainless steel, such as grade 316 stainless steel. However, those of ordinary skill in the art will appreciate that cell 101 and perforated plate 104 and piston 105 may also be formed from other materials capable of withstanding the pressures and temperatures used in drilling fluid tests. For example, according to API recommended practices, a filtration cell used in conventional drilling fluid high-pressure tests should be able to withstand working pressures of up to 1300 psi. Thus, drilling fluid test device 100 may include components capable of withstanding similar pressures.

Figure 3:
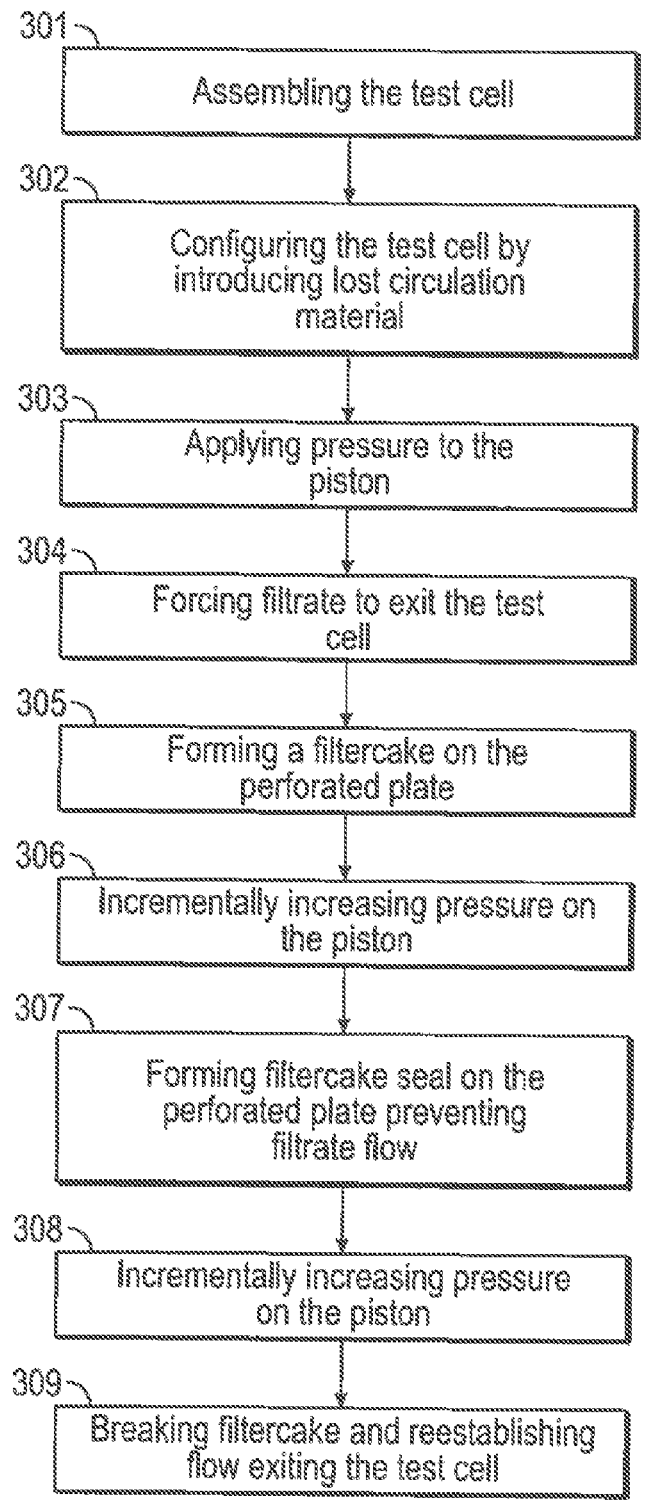
FIG. 3 is a flow diagram for a method of using a fluid test system in accordance with the present disclosure.

FIG. 3 shows a flow diagram of a method of testing a well fluid according to embodiments of the present disclosure. Referring to FIGS. 1 and 3 together, test cell 101 is assembled 301 and configured for testing by filling the first chamber 106 with LCM testing fluid 302. The assembling the test cell 301 may further include disposing the piston 15 in the body of test cell 101 proximate the second end 101 to form a second chamber 107 and disposing the perforated plate in the body of test cell 101 proximate the first end 102 to form a first chamber 106 and third chamber 113. The ends of test cell 101 may then be sealed and coupled to the appropriate pumps and collection vessels as described above. If the test cell 101 is configured such that the first chamber 106 is easily accessible through the first end 102, then the LCM fluid may be deposited directly into the first chamber 106 through the opening near first end 102 prior to sealing the test cell 101. Alternatively, if test cell 101 is configured such that perforated plate 104 is not removable, LCM may be introduced to the first chamber 106 via second fluid inlet 111 following sealing the test cell 101.

Once the test cell 101 is assembled 301 and has been configured by filling the central chamber with LCM fluid 302, a pressure may be applied to the piston 303. As mentioned above, first fluid inlet 109 may be in communication with pump 110. Thus, pump 110 may introduce fluid into second chamber 107 through first fluid inlet 109. The introduction of the fluid into second chamber 107 will exert a pressure on piston 105 causing piston 105 to translate from second end 103 toward first end 102 within the test cell 101. The pressure exerted on piston 105 is not meant to be limited to a force caused by the introduction of fluid into second chamber 107. Any ordinary means of exerting a force on a plate, for example, a spring or bellows may be used without departing from the scope of the disclosure. In some embodiments, a pressure monitoring device known to one of ordinary skill in the art may be coupled to test cell 101 to monitor changes in pressure.

The translational movement of piston 105 in test cell 101 forces the LCM test fluid to be pushed through perforated plate 104. During testing, a perforated plate may be selected to model downhole conditions such that an appropriate LCM may be selected. As LCM fluid is forced through perforated plate 104 some of the LCM will form a deposit 305 on perforated plate 104 and the remaining LCM will exit test cell 101 as filtrate 304 through filtrate outlet 108. A flow meter, pressure sensor, or any similar device used by individuals skilled in the art to monitor fluid properties may be coupled to filtrate outlet 108. In certain embodiments the filtrate may be directed to a filtrate collection vessel 114, which may also be coupled to sensors configured to measure fluid properties. Fluid properties that may be measured may include, for example, volume, density, and composition.

In one embodiment, during operation of the fluid testing device 100, the pressure exerted on piston 105 may be incrementally increased 306 by pump 110 introducing more fluid into chamber 107. This incremental increase in pressure may be performed manually by a technician or automatically by a central control unit. For each incremental increase in pressure, data regarding filtrate properties may be recorded such that a relationship between filtrate properties and pressure may be determined. Specifically, the relationship between the flow rate of the filtrate and pressure may be determined by this data such that an operable pressure range for filtercake formation can be determined.

Pressure exerted on piston 105 may be increased until filtrate no longer exits through filtrate outlet 108. At this point the deposit on perforated plate 104 has formed a seal 307. This pressure is the lower threshold at which a deposit is formed for a particular LCM and perforated plate combination. After determining this lower threshold an upper threshold at which the deposit breaks and filtrate once again exits test cell 101 through filtrate outlet 108 may be determined. Here, the pressure is incrementally increased 308, for example, by 5, 10, 15, 20 psi increments or other incrememnts, until the seal of the deposit breaks and flow through filtrate outlet 108 is once again established 309. Thus, the pressure range of deposit formation is determined for a particular LCM and perforated plate combination.

It may be helpful to use some embodiments of the test device system described above while simultaneously pumping a fluid downhole, which may be performed, for example, on a rig. While pumping a fluid downhole, fluid loss may occur due to pores in the rock formation. In order to evaluate the suitability of an LCM to run downhole or perforated plate, downhole pressure conditions may be determined or estimated for a particular application. A perforated plate with perforations that simulate the formation being drilled may be selected and assembled into a test cell. Various LCM materials may then be selected and tested in the test cell, as described above with respect to FIG. 3. In addition, parameters relating to pressure exerted on piston 105 and filtrate properties may be obtained and correlated to pressure. The data may be obtained and analyzed manually by a technician on hand. In other embodiments, a central control unit may be used to automate the data collection and analysis. The analysis may include a comparison of downhole pressure conditions to the pressure data collected by the fluid testing system. If the pressure range of filtercake formation as indicated by the data falls within a working range of the present downhole conditions, the LCM may be selected.

While drilling on, for example, a rig it may be useful to immediately select an LCM suited to run downhole given present conditions. In such a situation, after pumping a fluid downhole and determining fluid loss of the fluid being pumped downhole, a suitable LCM may be selected using the methods described above. Specifically, once the current downhole pressures are determined, the steps of the method described by FIG. 3 may be carried out using the fluid testing system 100 of FIG. 1. Here, an appropriate perforated plate 104 to reflect the fractures present in the rock formation being drilled is selected. At least one LCM may be tested using the system and method of FIGS. 1 and 3. If more than one LCM is tested, the lower pressure threshold of when a deposit forms and the upper pressure threshold, when the seal of the deposit breaks, may be compared to the current downhole conditions. The LCM that provides the most desirable pressure characteristics for the current downhole conditions may be selected to run downhole and mitigate fluid loss.

Although only a few example embodiments have been described in detail above, those skilled in the art will readily appreciate that many modifications are possible in the example embodiments without materially departing from the apparatus, systems, and methods disclosed herein. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. §112, paragraph 6 for any limitations of any of the claims herein, except for those in which the claim expressly uses the words 'means for' together with an associated function.

What is claimed is:

1. A system comprising:
   a test cell comprising:
      a perforated plate disposed proximate a first end of the test cell, the perforated plate comprising at least one perforation spanning a substantial majority of the chord along which it lies;
      a piston disposed within the test cell;
      a first chamber formed between the perforated plate and the piston, the first chamber configured to receive lost circulation material (LCM);
      a second chamber formed between the piston and a second end of the test cell, the piston providing a seal between the first and second chambers;
      a fluid inlet disposed proximate the second end of the test cell configured to introduce fluid into a second chamber of the test cell;
      a filtrate outlet disposed proximate the first end of the test cell to discharge filtrate;
      a pump in communication with the fluid inlet; and
   a central control unit coupled to the test cell configured to monitor a pressure in the second chamber and a flow rate at the filtrate outlet and provide instructions to the pump based on the pressure and the flow rate.

2. The system of claim 1, further comprising a fluid inlet configured to introduce fluid to the first chamber.

3. The system of claim 1, wherein the perforated plate includes at least one slot, the at least one slot having a width ranging from about 1 mm to 5 mm.

4. The system of claim 1, further comprising a pressure measuring device coupled to the pump.

5. The system of claim 1, further comprising a filtrate collection vessel in communication with the filtrate outlet.

6. The system of claim 1, further comprising at least one of a volume measuring device, a flow meter, or pressure sensor coupled to the filtrate outlet.

7. The system of claim 1, wherein the central control unit is further configured to provide instructions to the apparatus for testing fluids at a drilling location.

8. The system of claim 1, further comprising a spacer ring disposed between the perforated plate and the filtrate outlet, wherein the spacer ring interfaces an inner surface of a body of the test cell.

9. The system of claim 8, further comprising a third chamber formed between the perforated plate and the first end of the test cell.

10. A method of testing well fluid comprising:
   filling a first chamber of test cell with lost circulation material ("LCM");
   applying a first pressure to a piston in the test cell by introducing fluid into a second chamber of a test cell wherein the first chamber and the second chamber are separated by the piston;
   wherein the first pressure forces a filtrate to exit the test cell through a perforated plate within the first chamber and forms a seal by depositing the LCM on the perforated plate;
   incrementally increasing pressure on the piston until the seal breaks at a second pressure; and
   determining a relationship between a flow rate of the filtrate and the increasing pressure.

11. The method of claim 10, wherein the first or pressure is a lower threshold, and the second pressure is an upper threshold.

12. The method of claim 10, further comprising directing the filtrate to a filtrate collection vessel.

13. The method of claim 10, further comprising:
   monitoring at least one filtrate property of volume and material composition of the filtrate; and
   analyzing the at least one filtrate property a function of pressure.

14. The method of claim 10, further comprising automatically testing the well fluid, the automatically testing comprising:
   sending a signal from a pressure sensor coupled to the test cell to the central control unit, sending a signal from a filtrate monitoring device to the central control unit; and
   sending a signal from a central control unit to a pump in communication with the second chamber.

15. The method of claim 10, wherein
   the first chamber is between the perforated plate proximate a first end of the test cell and the piston; and
   the second chamber is between the piston and a second end of the test cell.

16. The method of claim 15, wherein applying the first pressure to the piston Ante comprises:
   maintaining a higher pressure in the second chamber than the first chamber.

17. The method of claim 10, further comprising monitoring changes in the pressure applied to the piston.

18. The method of claim 17, wherein the pressure of the second chamber is monitored with a transducer.

\* \* \* \* \*